(12) United States Patent
Khosla et al.

(10) Patent No.: US 6,500,960 B1
(45) Date of Patent: *Dec. 31, 2002

(54) METHOD TO PRODUCE NOVEL POLYKETIDES

(75) Inventors: Chaitan Khosla, Stanford, CA (US); Rembert Pieper, Washington, DC (US); Guanglin Luo, Madison, CT (US); David E. Cane, Providence, RI (US); Camilla Kao, Palo Alto, CA (US)

(73) Assignees: Stanford University (Board of Trustees of the Leland Stanford Junior University), Stanford, CA (US); Brown University Research Foundation, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/311,756

(22) Filed: May 14, 1999

Related U.S. Application Data

(63) Continuation of application No. 09/164,306, filed on Oct. 1, 1998, which is a continuation-in-part of application No. 08/896,323, filed on Jul. 17, 1997, which is a continuation-in-part of application No. 08/675,817, filed on Jul. 5, 1996

(60) Provisional application No. 60/003,338, filed on Jul. 6, 1995.

(51) Int. Cl.[7] .......................................... C07D 493/00
(52) U.S. Cl. ................................................. 549/264
(58) Field of Search ........................................ 549/264

(56) References Cited

U.S. PATENT DOCUMENTS

| | | | |
|---|---|---|---|
| 4,551,433 A | 11/1985 | DeBoer | 435/253 |
| 4,874,748 A | 10/1989 | Katz et al. | 514/29 |
| 4,935,340 A | 6/1990 | Baltz et al. | 435/6 |
| 5,063,155 A | 11/1991 | Cox et al. | 435/76 |
| 5,098,837 A | 3/1992 | Beckmann et al. | 435/172.3 |
| 5,149,639 A | 9/1992 | Katz et al. | 435/76 |
| 5,168,052 A | 12/1992 | Cox et al. | 435/72 |
| 5,252,474 A | 10/1993 | Gewain et al. | 435/172.3 |
| 5,475,099 A | 12/1995 | Knauf et al. | |
| 5,514,544 A | 5/1996 | Rao et al. | 435/6 |
| 5,672,491 A | 9/1997 | Khosla et al. | 435/148 |
| 5,712,146 A | 1/1998 | Khosla et al. | 435/252.35 |
| 5,824,513 A | 10/1998 | Katz | |
| 5,876,991 A | 3/1999 | DeHoff et al. | 435/183 |
| 5,945,320 A | 8/1999 | Burgett et al. | 435/183 |
| 6,004,787 A | 12/1999 | Katz et al. | 435/183 |
| 6,060,234 A | 5/2000 | Katz et al. | 435/4 |
| 6,066,721 A | 5/2000 | Khosla et al. | 536/23.1 |
| 6,063,561 A | 6/2000 | Katz et al. | 435/4 |
| 6,080,555 A | 6/2000 | Khosla et al. | 435/41 |
| 6,200,813 B1 | 3/2001 | Katz et al. | 435/477 |
| 6,271,255 B1 | 8/2001 | Leadlay et al. | 514/450 |

FOREIGN PATENT DOCUMENTS

| | | |
|---|---|---|
| EP | 791655 | 8/1997 |
| EP | 791656 | 8/1997 |
| WO | WO 93/13663 | 7/1993 |
| WO | WO 95/08548 | 3/1995 |
| WO | WO 96/40968 | 12/1996 |
| WO | WO 97/02358 | 1/1997 |
| WO | WO 97/13845 | 4/1997 |
| WO | WO 98/01546 | 1/1998 |
| WO | WO 98/01571 | 1/1998 |

OTHER PUBLICATIONS

Brown et al., J. Chem. Soc. Chem. Commun. (1995) 15:1517–1518.
Cane et al., J. Antibiotics (1995) 48:647–651.
Dalbie–McFarland et al., Proc. Natl. Acad. Sci. USA (1982) 79:6409.
Donadio et al., Industrial Microorganism, Basic and Applied Molecular Genetics, R. H. Baltz, G.D. Hegeman and PIL. Skatrud (eds) (Amer. Soc. Microbial.), Washington, D.C. (1993) pp. 257–265.
Evans et al., J. Am. Chem. Soc. (1992) 114:9434–9453.
Floss, Tetrahydron (1991) 47(31):6045–6058.
Fu, Biochemistry (1994) 33(31):9321–9326.
Geisselsoder et al., BioTechniques (1987) 5:786.
Gokhale et al., Biochemistry (1998) 37:2524–2528.
Gordon et al., Acc. Chem. Res. (1996) 29(3):144–154.
Hamilton et al., J. Bacteriol. (1989) 171:4617.
Hershberger et al. (1989) "Genetics and Molecular Biology of Industrial Microorganisms," Am. Soc. for Microbiol. (Washington, DC) pp. 68–84.
Hopwood et al., Phil. Trans. R. Soc. Lond. B (1989) 324:549–562.

(List continued on next page.)

Primary Examiner—Amelia Owens
(74) Attorney, Agent, or Firm—Morrison & Foerster LLP

(57) ABSTRACT

Modified PKS gene clusters which produce novel polyketides in an efficient system in a host cell or in a cell free extract are described. The novel polyketides result from the incorporation of diketides of the formula

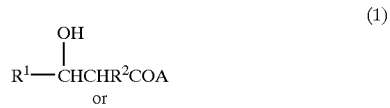

(1)

or

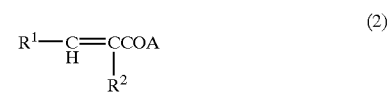

(2)

wherein A is a moiety that activates the diketide, and at least one of $R^1$ and $R^2$ is a substituent other than that natively occurring in the diketide normally processed by the modified PKS cluster. The polyketides may also be glycosylated to provide antibiotics.

17 Claims, 5 Drawing Sheets

OTHER PUBLICATIONS

Hutchinson, Bio/Technology (1994) 12:375–380.
Ireland et al., J. Org. Chem. (1980) 45:1868–1880.
Jay et al., J. Biol. Chem. (1984) 259:6311–6317.
Kao et al., J. Am. Chem. Soc. (1994) 16:11612–11613.
Katz et al., Ann. Review Microbiol. (1993) 47:875–912.
Khosla et al., Molec. Microbiol. (1992) 6(12):3237–3249.
Khosla et al., Tibtech (1996) 14:335–341.
Kunkel, Proc. Natl. Acad. Sci. USA (1985) 82:488.
Lambalot et al., J. Antibiotics (1992) 45:1981–1982.
Lehrer et al., J. Immun. Meth. (1991) 137:167–173.
MacNeil et al., Gene (1992) 115:119–125.
Malpartida et al., Nature (1987) 325(6107):818–821.
Marsden et al., Science (1998) 279:199–202.
Martin et al., J. Am. Chem. Soc. (1997) 119:3193.
Masamune et al., J. Am. Chem. Soc. (1975) 97:3512–3513.
Masumoto et al., Tetrohedron Lett. (1988) 29:3575.
McAlpine et al., The Journal of Antibiotics (1987) 40(8):1115–1122.
McDaniel et al., Science (1993) 262:1546–1550.
Perun, Drug Action and Drug Resistance in Bacteria, vol. 1, S. Mitsuhashi (ed). Univ. Park Press, Baltimore, 1977.
Roberts et al., Biochem. Soc. Transactions (1992) 21:32S.
Roberts et al., Eur. J. Biochem. (1993) 214:305–311.
Robinson, Phil. Trans. R. Soc. Lond. B (1991) 332:107–114.
Rohr, Angew. Chem. Int. Ed. Engl. (1995) 34(8):881–886.
Ruan et al., J. of Bacteriology (1997) 79(20):6416–6425.
Rudd et al., J. Gen. Microbiol. (1979) 114:35–43.
Strohl et al., Molecular Microbiology (1992) 6(2):147–152.
Strohl et al., Society of Industrial Microbiology (1991) 7:163–174.
Toshima et al., J. Am. Chem. Soc. (1995) 117:3717.
Tsoi et al., Chemistry & Biology (1985) 2:355–362.
Tuan et al., Gene (1990) 90:21.
Vedejs et al., J. Am. Chem. Soc. (1987) 109:5437–5446.
Vedejs et al., J. Am. Chem. Soc. (1989) 111:8430–8438.
Bedford, D., et al., Chemistry & Biology (1996), 3(10):827–831.
Daum, S.J., et al., Ann Rev Microbiol (1979), 33:241–265.
Donadio, S., et al., Proc Natl Acad Sci USA (1993), 90:7119–7123.
Dutton, C.J., et al., Tetrahedron Letters (1994), 35(2):327–330.
Kao, C.M., et al., J Am Chem Soc (1995), 117(35):9105–9106.
Kao, C.M., et al., J Am Chem Soc (1996), 118(38):9184–9185.
Kao et al., Biochemistry, vol. 35, No. 38, 1996, 1966 Amer. Chem. Society, pp: 12363–12368.
Kao, C.M., et al., J Am Chem soc (1997), 119(46):11339–11340.
Kuhstoss, S., et al., Gene (1996), 183:231–236.
Kramer, P.J., et al., J Am Chem Soc (1997), 119(4):635–639.
McDaniel, R., et al., J. Am Chem Soc (1997), 119(18):4309–4310.
Oliynyk, M., et al., Chemistry & Biology (1996) 3(10):833–839.
Pieper, R., et al., J Am Chem Soc. (1995), 1174(45)11373–4.
Pieper, R., et al., Nature (1995), 378:263–266.
Pieper, R., et al., Biochemistry (1996), 35:2054–2060.
Pieper, R., et al., Biochemistry (1997), 36(7):1846–1851.
Wiesmann, K.E.H., et al., Chemistry & Biology (1995), 2(9):583–9.

Dutton et al., "Novel Avermectins Produced by Mutational Biosynthesis," The Journal of Antibiotics, vol. 44, No. 3, pp:357–65 (1991).
Kao et al., "Evidence for Two Catalytically Independent Clusters of Active Sites in a Functional Modular Polyketide Synthase," Biochemistry, vol. 35, No. 38, 1996, 1966 American Chemical Society, pp: 12363–8.
Doishio et al., "Gene," 115, (1992), pp: 97–103.
Kao et al., "Science," 265 (1994), pp: 509–11.
Pieper, R., et al., "Remarkable Broad Substrate Specificity of a Modular Polyketide Synthase in a Cell–Free System," J Am Chem Soc. (1995) 1174(45)11373–4.
Pieper, R., et al., "Cell–free synthesis of polyketides by recombinant erythromycin polyketide synthesis," Nature (1995) 378:263–6.
Pieper, R., et al., "Erythromycin Biosynthesis: Kinetic Studies on a Fully Active Modular Polyketide Synthase Using Natural and Unnatural Substrates," Biochemistry (1996) 35:2054–60.
Pieper, R., et al., "Purification and characterization of Bimodular and Trimodular Derivatives of the Erythromycin Polyketides Synthase," Biochemistry (1997) 36(7):1846–51.
Daum, S.J., et al., "Mutational Biosynthesis of New Antibiotics," Ann Rev Microbiol (1979) 33:241–65.
Dutton, C.J., et al., "Avermectin Biosynthesis. Intact Incorporation of a Diketide Chain–Assembly Intermediate into the Polyketide Macrocycle Ring," Tetrahedron Letters (1994) 35(2):327–30.
McDaniel, R., et al., "Gain–of–Function Mutagenesis of a Modular Polyketide Synthase," J. Am Chem Soc (1997) 119(18):4309–10.
Kramer, P.J., et al., "Rational Design and Engineered Biosynthesis of a Novel 18–Carbon Aromatic Polyketide," J Am Chem Soc (1997) 119(4):635–9.
Kao, C.M., et al., "Gain of Function Mutagenesis of the Erythromycin Polyketide Synthase. 2. Engineered Biosynthesis of an Eight–Membered Ring Tetraketide Lactone," J Am Chem soc (1997) 119(46):11339–40.
Wiesmann, K.E.H., et al., "Polyketide synthesis in vitro on a modular polyketide synthase," Chemistry & Biology (1995) 2(9):583–9.
Kao, C.M., et al., "Manipulation of Macrolide Ring Size by Directed Mutagenesis of a Modular Polyketide Synthase," J Am Chem Soc (1995) 117(35):9105–6.
Kao, C.M., et al., "Engineered Biosynthesis of Structurally Diverse Tetraketides by a Trimodular Polketide Synthase," J Am Chem Soc (1996) 118(38):9184–5.
Donadio, S., et al., "Modular Organization of Genes Required for Complex Polyketide Biosynthesis," Science (1991) 252:675–9.
Donadio, S., et al., "An erythromycin analog produced by reprogramming of polyketide synthesis," Proc Natl Acad Sci USA (1993) 90:7119–23.
Bedford, D., et al., "A functional chimeric modular polyketide synthase generated via domain replacement," Chemistry & Biology (1996) 3(10):827–31.
Oliynyk, M., et al., "A hybrid modular polyketide synthase obtained by domain swapping," Chemistry & Biology (1996) 3(10):833–9.
Kuhstoss, S., et al., "Production of a novel polyketide through the construction of a hybrid polyketide synthase," Gene (1996) 183:231–6.

Aparicio et al., "Limited Proteolysis and Active–Site Studies of the First Multienzyme Component of the Erythromycin–Producing Polyketide Synthase," (1994) J. of Biol. Chem. 269(11):8524–8.

Bartel et al., "Biosynthesis of Antraquinones by Interspecies Cloning of Actinorhodin Biosynthesis Genes in Streptomycetes: Clarification of Actinorhodin Gene Functions," (1990) J. Bacteriol. 172(9):4816–26.

Beck et al., "The Multifunctional 6–methylsalicylic Acid Synthase Gene of Penecillium Patulum. Its Gene Structure Relative to that of Other Polyketide Synthases," (1990) Eur. J. Biochem. 192:487–98.

Bevitt et al., "6–Deoxyerythronolide–B Synthase 2 from *Saccharopolyspora erythaea*: Cloning of the Structural Gene, Sequence Analysis and Inferred Domain Structure of the Multifuncitonal Enzyme," (1992) Eur. J. Biochem. 204:39–49.

Bibb et al., "Analysis of the Nucleotide Sequence of the Streptomyces Glaucescens tcml Genes Provides Key Information about the Enzymology of Polyketide Antibiotic Biosynthesis," (1989) EMBO J. 8(9):2727–36.

Caballero et al., "Organisation and Functions of the actVA Region of the Actinorhodin Biosynthetic Gene Cluster of *Streptomyces coelicolor*," (1991) Mol. Gen. Genet. 230:401–12.

Caffrey et al., "An Acyl–Carrier–Protein—Thioesterase Domain from the 6–Deoxyerythronolide B Synthase of *Saccharopolyspora erythraea*. High–Level Production, Purification and Characterisation in *Escherichia coli*," (1991) Eur. J. Biochem. 195:823–30.

Caffrey et al., "Identification of DEBS 1, DEBS 2 and DEBS 3, the Multienzyme Polypeptides of the Erythromycin–Producing Polyketide Synthase from *Saccharopolyspora erythraea*," (1992) FEBS Lett. 304:225–8.

Corcoran et al., "The Biogenesis of Fatty Acids and Erythronolide–Like Substances in Mycelium–Free Extracts of *Streptomyces erythreus*," (1967) in 5th International Congress of chemotherapy, Vienna, Abstracts of Communications, pp:35–40.

Corcoran, ed. in *Antibiotics vol. IV Biosynthesis*, Springer–Verlag, New York, pp:145–50 (1982).

Cortes et al., "An Unusually Large Multifunctional Polypeptide in the Erythromycin–Producing Polyketide Synthase of *Saccharopolyspora erythraea*," (1990) Nature 348:176–8.

Davis et al., "Functional Mapping of a Polyketide Synthase from aspergillus terreus Involved in Lovastain Synthesis," (1994) Abst. of the Genetics of Industrial Microorganisms Mtg. P288:192.

Dimroth et al., "Biosynthese von 6–Methylsalicylsaure," (1970) Eur. J. Biochem. 13:98–110.

Donadio et al., "Modular Organization of Genes Required for Complex Polyketide Biosynthesis," (1991) Science 252:675–9.

Donadio et al., "Organization of the Enzymatic Domains in the Multifunctional Polyketide Synthase Involved in Erythromycin Formation in *Saccharopolyspora erythraea*," (1992) Gene 111:51–60.

Fernandez–Moreno et al., "The act Cluster Contains Regulatory and Antibiotic Export Genes, Direct Targets for Translational Control by the bldA tRNA Gene of Streptomyces," (1991) Cell 66:769–80.

Fernandez–Moreno et al., "Nucleotide Sequence and Deduced Functions of a Set of Cotranscribed Genes of *Streptomyces coelicolor* A3(2) Including the Polyketides Synthase for the Antibiotic Actinorhodin," (1992) J. Biol. Chem. 267:19278–90.

Hallam et al., "Nucleotide Sequence, Transcription and Deduced Function of a Gene Involved in Polyketide Antibiotic Synthesis in *Streptomyces coelicolor*," (1988) Gene 74:305–20.

Hopwood et al., "Product for 'Hybrid' Antibiotics by Genetic Engineering," (1985) Nature 314(6012):642–4.

Hopwood et al., "Genes for Polyketide Secondary Metabolic Pathways in Microorganisms and Plants," (1992) Secondary Metabolites: Their Function and Evolution, Wiley Chichester (Ciba Foundation Symposium 171), pp:88–112.

Hunaiti et al., "Source of Methylmalonyl–Coenzyme A for Erythromycin Synthesis: Methylmalonyl–Coenzyme A Mutase from *Streptomyces erythreus*," (1984) Antimicrobial Agents and Chemotherapy 25(2):173–8.

Kao et al., "Engineered Biosynthesis of a Complete Macrolactone in a Heterologous Host," (1994) Science 265:509–12.

Khosla et al., "Genetic Construction and Functional Analysis of Hybrid Polyketide Synthases Containing Heterologous Acyl Carrier Proteins," (1993) J. Bacteriol. 175(8):2197–204.

Lanz et al., "The Role of Cysteines in Polyketides Synthase," (1991) J. of Biol. Chem. 266(15):9971–6.

Leadlay et al., "The Erythromycin–Producing Polyketide Synthase," (1993) Biochem. Soc. Transactions 21:218–22.

MacNeil et al., "Complex Organization of the *Streptomyces avermitilis* Genes Encoding the Avermectin Polyketide Synthase," (1992) Gene 115:119–25.

Malpartida et al., "Molecular Cloning of the Whole Biosynthetic Pathway of a Streptomyces Antibiotic and its Expression in a Heterologous Host," (1984) Nature 309:462–4.

Malpartida et al., "Physical and Genetic Characertisation of the Gene Cluster for the Antiobiotic Actinorhodin in *Streptomyces coelicolor* A3(2)," (1986) Mol. Gen. Genet. 205:66–73.

Marsden et al., "Stereospecific Acyl Transfers on the Erythromycin–Producing Polyketide Synthase," (1994) Science 263:378–80.

Roberts et al., "[$^3$H]Tetrahydrocerulenin, a Specific Reagent for Radio–Labeling Fatty Acid Synthases and Related Enzymes," (1983) FEBS Lett. 1591(1, 2):13–6.

Roberts et al., "Use of [$^3$H]Tetrahydrocerulenin to Assay Condensing Enzyme Activity in *Streptomyces erythreus*," (1984) Biochem. Soc. Transactions 12:642–3.

Shen et al., "Enzymatic Synthesis of a Bacterial Polyketide from Acetyl and Malonyl Coenzyme A," (1993) Science 262:1535–40.

Sherman et al., "Structure and Deduced Function of the Granaticin–Producing Polyketide Synthase Gene Cluster of *Streptomyces violaceruber* T022," (1989) EMBO J. 8(9):2717–25.

Sherman et al., "Functional Replacement of Genes for Individual Polyketide Synthase Components in *Streptomyces coelicolor* A3(2) by Hetergenous Genes from a Different Polyketide Pathway," (1992) J. Bacteriol. 174(19):6184–90.

Spencer et al., "Purification and Properties of 6–Methylsalicylic Acid Synthase from *Penicillium patulum*," (1992) Biochem. J. 288:839–46.

Wawszkiewicz et al., "Propionyl–CoA Dependent $H^{14}CO_3^-$ Exchange into Methylmalonyl–CoA in Extracts of *Streptomyces erythraeus*," (1964) Biochemische Zeitschrift 340:213–27.

Cane et al., (1993) "Macrolide biosynthesis. 7. Incorporation of polyketide chain elongation intermediates into methymycin," J. Am. Chem. Soc. 115:522–6.

Kao C.M., et al., (1994) "Engineered biosynthesis of a complete macrolactone in a heterologous host," Science 265:509–12.

Donadio S., et al., (1992) "Biosynthesis of the erythromycin macrolactone and a rational approach for prodrug hybrid macrolides," Gene 115:97–103.

Omura et al., "Inhibition of the Biosynthesis of Leucomycin, a Macrolide Antibiotic, by Cerulenin," J. Biochem. 75:193–5 (1974).

METHOD TO PRODUCE NOVEL POLYKETIDES

CROSS REFERENCE TO RELATED APPLICATIONS

This application is a continuation application of U.S. Ser. No. 09/164,306, filed Oct. 1, 1998, which is a continuation-in-part of application Ser. No. 08/896,323, filed Jul. 17, 1997, which is a continuation-in-part of U.S. Ser. No. 08/675,817, filed Jul. 5, 1996, and also claims priority from PCT/US98/14911, filed Jul. 17, 1998. The contents of these applications are incorporated herein by reference and from Provisional application 60/003,338 filed Jul. 6, 1995.

STATEMENT OF RIGHTS TO INVENTIONS MADE UNDER FEDERALLY SPONSORED RESEARH

This invention was made with U.S. government support from the National Institutes of Health (GM22172 and CA66736-01). The government has certain rights in this invention.

TECHNICAL FIELD

The invention relates to methods to synthesize polyketides which are novel using modified modular polyketides synthases (PKS) which cannot utilize a natural first module starter unit.

BACKGROUND ART

Modular polyketide syntheses are typified by the organization of deoxyerythronolide B synthase (DEBS) which produces β-deoxyerythronolide B (6-dEB) the parent macrolactone of the broad spectrum antibiotic erythromycin. DEBS consists of three large polypeptides each containing about 10 distinctive active sites. FIG. 1 shows, diagrammatically, the nature of the three DEBS modules encoded by the three genes eryAI, eryAII and eryAIII.

Various strategies have been suggested for genetic manipulation of PKS to produce novel polyketides. New polyketides have been generated through module deletion (Kao, C.M. et al., *J. Am. Chem. Soc.* (1995) 117:9105–9106; Kao, C.M. et al, *J. Am. Chem. Soc.* (1996) 118:9184–9185). Also reported to provide novel polyketides are loss of function mutagenesis within reductive domains (Donadio, S. et al., *Science* (1991) 252:675–679; Donadio, S. et al, *Proc. Natl. Acad. Sci. USA* (1993) 90:7119–7123; Bedford, D. et al., *Chem. Biol.* (1996) 3:827–831) and replacement of acyl transferase domains to alter starter or extender unit specificity (Oliynyk, M et al., *Chem. Biol.* (1996) 3:833–839; Kuhstoss, S. eT al., *Gene* (1996)183:231–236), as well as gain of function mutagenesis to introduce new catalytic activities within existing modules (McDaniel, R. et al., *J. Am. Chem. Soc.* (1997) in press). In some of these reports, downstream enzymes in the polyketide pathway have been shown to process non-natural intermediates. However, these methods for providing novel polyketides suffer from the disadvantages of requiring investment in cloning and DNA sequencing, the systems used being limited to producer organisms for which gene replacement techniques have been developed, primer and extender units that can only be derived from metabolically accessible CoA thioesters, and the fact that only limited auxiliary catalytic functions can be employed.

The DEBS system in particular has been shown to accept non-natural primer units such as acetyl and butyryl-CoA (Wiesmann, KEH et al., *Chem. Biol.* (1995) 2:583–589; Pieper, R. et al., *J. Am. Chem. Soc.* (1995) 117:11373–11374) as well as N-acetylcysteamine (NAC) thioesters of their corresponding diketides (Pieper, R et al., *Nature* (1995) 378:263–266). However, it has become clear that even though such unnatural substrates can be utilized, competition from the natural starter unit has drastically lowered yield. Even if starter units are not supplied artificially, they can be inherently generated from decarboxylation of the methylmalonyl extender units employed by the DEBS system (Pieper, R. et al., *Biochemistry* (1996) 35:2054–2060; Pieper, R et al., *Biochemistry* (1997) 36:1846–185 1).

Accordingly, it would be advantageous to provide a mutant form of the modular polyketide synthesis system which cannot employ the natural starter unit. Such systems can be induced to make novel polyketides by supplying, instead, a suitable diketide as an NAC thioester or other suitable thioester. Mutations have been made in the past to eliminate the competition from natural materials (Daum, S.J. et al., *Ann. Rev. Microbiol.* (1979) 33:241–265). Novel avermectin derivatives have been synthesized using a randomly generated mutant strain of the avermectin producing organism (Dutton, C.J. et al., *Tetrahedron Letters* (1994) 35:327–330; Dutton, C.J. et al., J. Antibiot. (1991) 44:357–365). This strategy is, however, not generally applicable due to inefficiencies in both mutagenesis and incorporation of the substrates.

Thus, there is a need for a more efficient system to prepare novel polyketides by inhibiting competitive production of the natural product.

DISCLOSURE OF THE INVENTION

The invention is directed to methods to prepare novel polyketides using modified modular polyketide synthase systems wherein directed modification incapacitates the system from using its natural starting material. Novel polyketides can then be synthesized by overriding the starter module and supplying a variety of suitable diketide substrates.

Thus, in one aspect, the invention is directed to a method to prepare a novel polyketide which method comprises providing a thioester diketide substrate to a modular PKS comprising at least two modules under conditions wherein said substrate is converted by said modular PKS to a product polyketide, wherein said PKS has been modified to prevent its utilization of the native starter unit. In other aspects, the invention is directed to the modified modular PKS which is disarmed with respect to utilization of the native starter substrate supplying the initial two carbon unit, and to suitable cells modified to contain this disarmed PKS. The invention is further directed to recombinant materials for production of the modified PKS and to the novel polyketides produced by this system.

MODES OF CARRYING OUT THE INVENTION

Figure 1:
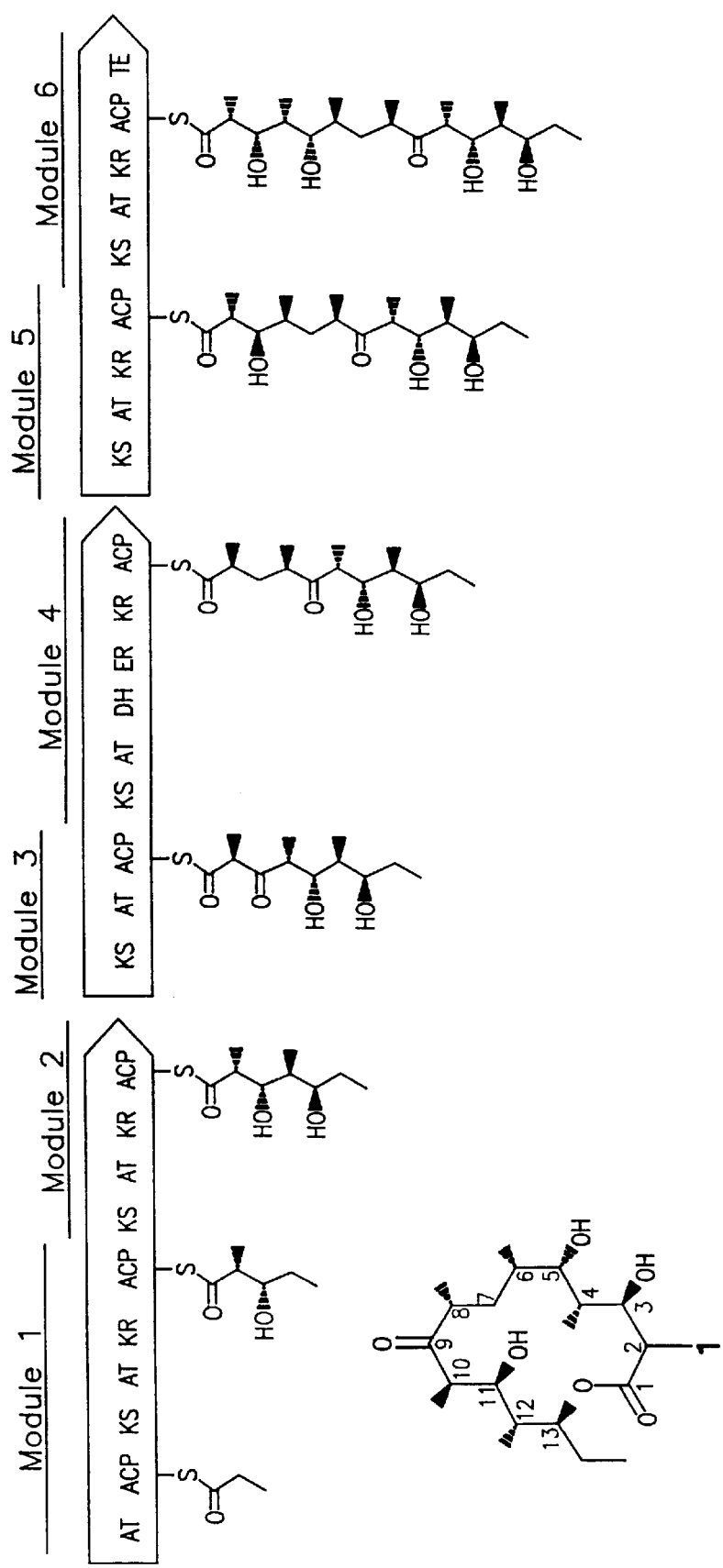
FIG. 1 shows a schematic representation of the DEBS modular PKS.

The invention provides modular PKS systems which are disarmed with respect to loading the native starting material and their corresponding genes. In a particularly preferred embodiment, the ketosynthase (KS) of module 1 is inactivated so as to prevent competition from the native starter unit. Other approaches to similarly disarming the PKS involve inactivating the acyl transferase (AT) or acyl carrier protein (ACP) finctions of module 1.

The PKS of the invention must contain at least two modules but may contain additional modules and, indeed be, represent complete synthase systems. While the DEBS PKS system is used to illustrate the invention, any modular PKS can be used, such as the modular PKS resulting in the production of avermectin, rapamycin and the like. Suitable mutations can be introduced by known site specific mutagenesis techniques.

Other micro-organisms such as yeast and bacteria may also be used. When host cells, such as bacteria, yeast, or even mammalian or insect cells, which normally do not produce polyketides are employed, it may be necessary to modify the hosts so as to provide posttranslational processing of the PKS enzymes. Specifically, in order to be functional, the ACP activities must be phosphopantetheinylated. This conversion of an apo-ACP to its activated form is accomplished by enzymes collectively referred to as holo-ACP synthases or PTrases. Forms of these enzymes which function in the fatty acid synthase pathways do not appear to be effective in providing holo-ACP functionalities in the PKS clusters. Thus, importation of a suitable synthase in a recombinant system when the polyketide synthesis is performed in whole cells other than, for example, streptomyces should be employed. If the synthesis is conducted in a cell-free system, the PKS enzymes utilized must have been synthesized under conditions where the holo-ACP synthase is present.

The novel polyketides may thus be synthesized in a suitable hosts, such as a Streptomyces host, especially a Streptomyces host modified so as to delete its own PKS, or other cells modified to produce a suitable PTTase if needed. The polyketides may also be synthesized using a cell-free system by producing the relevant PKS proteins recombinantly and effecting their secretion or lysing the cells containing them. A typical cell-free system would include the appropriate functional PKS, NADPH and an appropriate buffer and substrates required for the catalytic synthesis of polyketides. To produce the novel polyketides thioesters of the extender units are employed along with the thioester of a diketide.

The novel polyketides produced as a result of the modified PKS clusters will differ in the substituents that correspond to the residue of the starter unit in the finished polyketide. And, since the diketide intermediate is being supplied to the modified PKS cluster, the nature of the extender unit incorporated immediately adjacent the starter unit may also be varied. Thus, the diketides used to make the novel polyketides of the invention are of the general formulas

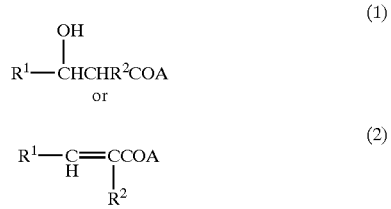

wherein A is a moiety that activates the diketide, typically a sulfhydryl such as the N-acetyl cysteamine thioester illustrated below, and at least one of $R^1$ and $R^2$ is a substituent other than that natively occurring in the diketide normally processed by the modified PKS cluster. In general, $R^1$ is a substituted or unsubstituted, saturated or unsaturated hydrocarbyl moiety (1–15C), said hydrocarbyl optionally containing one or two heteroatoms especially $N_1$ O or S and $R^2$ is a substituted or unsubstituted saturated or unsaturated hydrocarbyl moiety (1–4AC) or is OR, SR, or NHR, wherein R is substituted or unsubstituted, saturated or unsaturated hydrocarbyl of 1–4C. However, both $R^1$ and $R^2$ cannot be methyl and if $R^2$ is methyl, $R^1$ cannot be ethyl.

Typical substituents include halo, $OR^3$, $SR^3$, $NR_2$, $-OOCR^3$, $-NHOCR^3$, $R^3CO-$, $R^3COO-$ and $R^3CONH-$ wherein each $R^3$ is independently H or lower alkyl (4–4C).

The invention is also directed to polyketides which result from incorporating the diketides of formulas (1) or (2) and to glycosylated forms thereof.

The following examples are intended to illustrate but not to limit the invention.

PREPARATION A

Starting Materials

Streptomyces coelicolor CH999, which has been engineered to remove the native PKS gene cluster is constructed as described in WO 95/08548. pRM5, a shuttle plasmid used for expressing PKS genes in CH999 was also described in that application. Plasmid pCK7 which contains the entire DEBS modular system was described in the foregoing application as well.

EXAMPLE 1

Preparation of DEBS 1+2+TE

A modified DEBS PKS system containing only modules 1 and 2 and thioesterase (TE) activity, designated DEBS 1+2+TE, was subjected to site directed mutagenesis to inactivate module 1 KS by replacing the active site cysteine residue in the signature sequence in which a cysteine residue is followed by three consecutive serine residues followed by a leucine residue by alanine. The resulting expression plasmid, designated pKAO179, encodes a 2-module PKS which is inactive under the standard reaction conditions for synthesis of the native product, i.e., propionyl-CoA, methylmalonyl-CoA, and NADPH. The details of this construction are set forth in Kao, C.M. et al., Biochemistry (1996) 35:12363–12368. When provided with the diketide thioester (2S, 3R)-2-methyl-3-hydroxy-pentanoyl-N-acetylcysteamine thioester, and with methylmalonyt-CoA, and NADPH, the triketide product is obtained.

The triketide product is produced under these conditions when the PKS is incubated in a cell-free system or can be duplicated in vivo by providing the appropriate diketide thioester analogs to actively growing cultures of CH999 containing the modified expression plasmid.

A culture of S. coelicolor CH999/pKA0179 is established by inoculation of 200 mL of SMM medium (5% PEG-800, 0.06% $MgSO_4$, 0.2% $(NH_4)_2SO_4$, 25 mM TES, pH 7.02, 25 mM $KH_2PO_4$, 1.6% glucose, 0.5% casamino acids, trace elements) with spores. The culture is incubated at 30° C. with shaking at 325 rpm. A solution of (2S, 3R)-2-methyl-3-hydroxypentanoyl N-acetylcysteamine thioester (100 mg) and 4-pentynoic (15 mg) in 1 mL of methylsulfoxide is added to the culture in three parts: after 50 hours (400 μL); after 62 hours (300 μL); and after 86 hours (300 μL). After a total of 144 hours, the culture is centrifuged to remove mycelia The fermentation broth is saturated with NaCl and extracted with ethyl acetate (5×100 mL). The combined organic extract is dried over $Na_2SO_4$, filtered, and concentrated. Silica gel chromatography yields (2R, 3S, 4S, SR)-2,4-dimethyl-3,5-dihydroxy-n-heptanoic acid δ-lactone.

EXAMPLE 2

Preparation of Polyketides from the DEBS Cluster

The active site mutated module 1 KS domain of the eryAI (DEBS 1 gene) is provided on plasmid pCK7, (Kao, C.M et al., Science (1994) 265:409–412), which contains the eryAI, eryAII (DEBS 2) and eryAIII (DEBS 3 genes) under control of the actI promoter. Expression from this plasmid renamed pJRJ2 results in a suitably modified full length PKS system. pJRJ2 was transformed into CH999 and grown on R2YE medium. No detectable 6 DEB-like products were produced.

In more detail, lawns of CH999/pJRJ2 were grown at 30° C. on R2YE agar plates containing 0.3 mg/ml sodium propionate. After three days, each agar plate was overlayed with 1.5 mL of a 20 mM substrate solution in 9:1 water:DMSO. After an additional 4 days, the agar media (300 mL) were homogenized and extracted three times with ethyl acetate. The solvent was dried over magnesium sulfate and concentrated. Concentrated extracts were purified by silica gel chromatography (gradient of ethyl acetate in hexanes) to afford products.

However, when substrate 2, prepared by the method of Cane et al., J. Am. Chem. Soc. (1993) 115:522–526; Cane, D.E. et al., J. Antibiot. (1995) 48:647–651, shown in FIG. 2 (the NAC thioester of the native diketide) was added to the system, the normal product, 6 dEB was produced in large quantities. Administration of 100 mg substrate 2 to small scale cultures (300 ml grown on petri plates as described above) resulted in production of 30 mg 6 dEB, 18% yield.

EXAMPLE 3

Production of Novel Polyketides

Figure 2A:
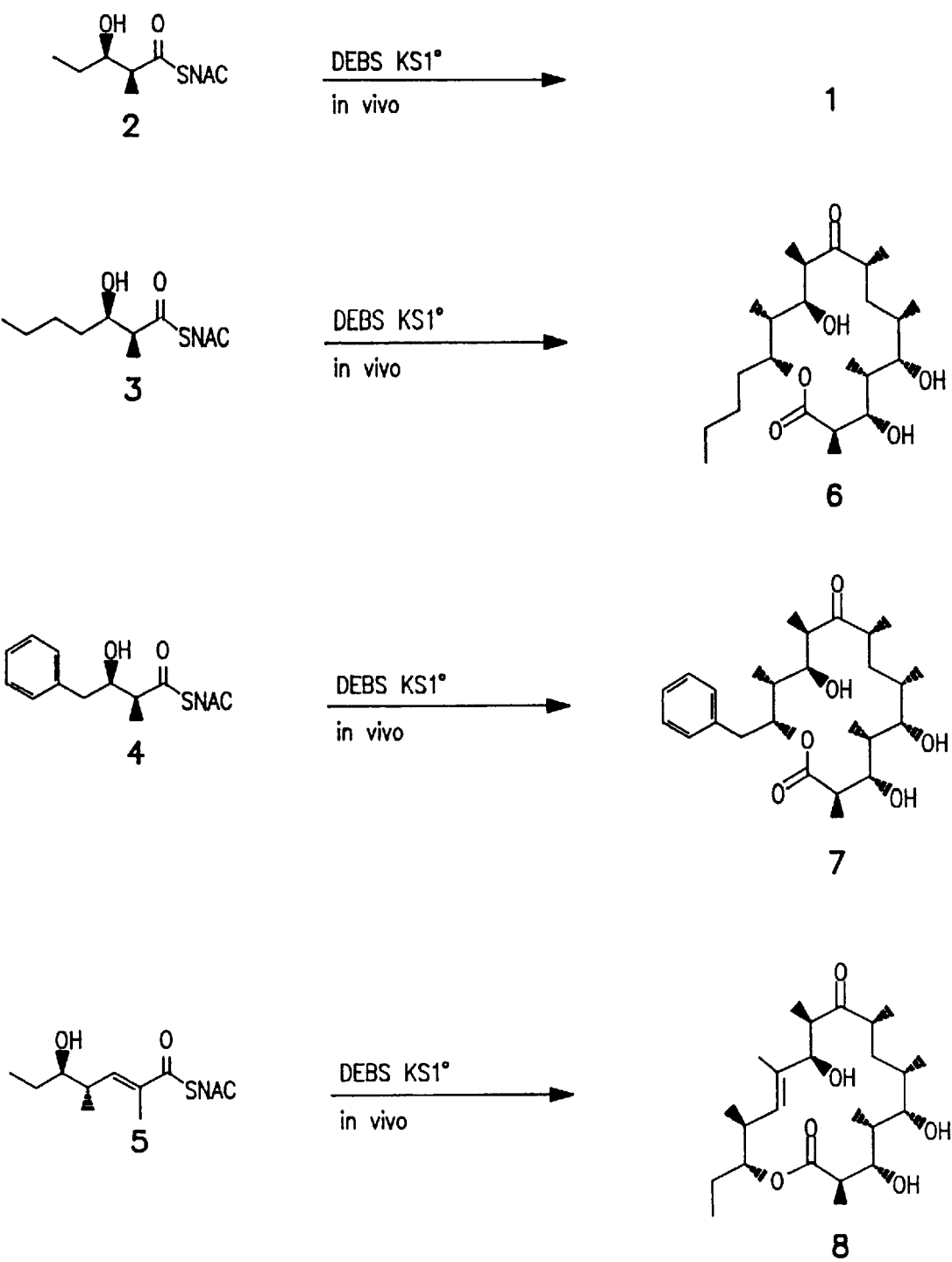
FIGS. 2A–2C show the products of a modified DEBS construct wherein the ketosynthase (KS) in module 1 is disarmed.

Diketides with the structures shown in FIG. 2A as formulas 3, 4, and 5 were then administered to growing cultures of CH999/pJRJ2 under the conditions of Example 2. Substrates 3 and 4 were prepared as described for Substrate 2 but substituting valeraldehyde and phenylacetaldehyde, respectively for propionaldehyde in the aldol reactions. The preparation of Substrate 5 was described by Yue, S. et al., J. Am. Chem. Soc. (1987) 109:1253–1255. Substrates 3 and 4 provided 55 mg/L of product 6 and 22 mg/L of product 7, respectively. Substrate 5 resulted in the production of 25 mg/L of the 16 member lactone 8, an unexpected product.

EXAMPLE 4

Additional Novel Polyketides

Figure 2B:
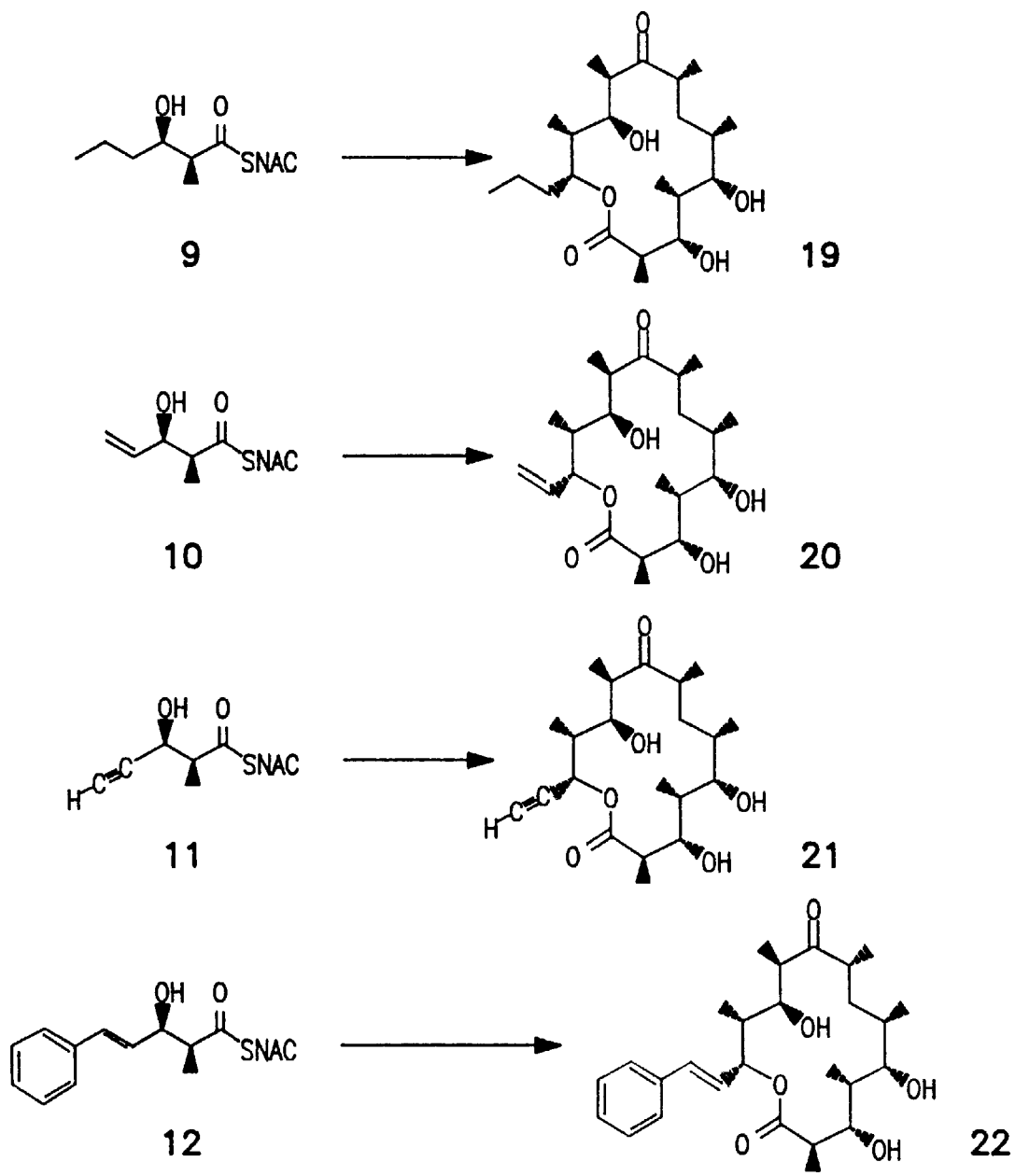
Figure 2C:
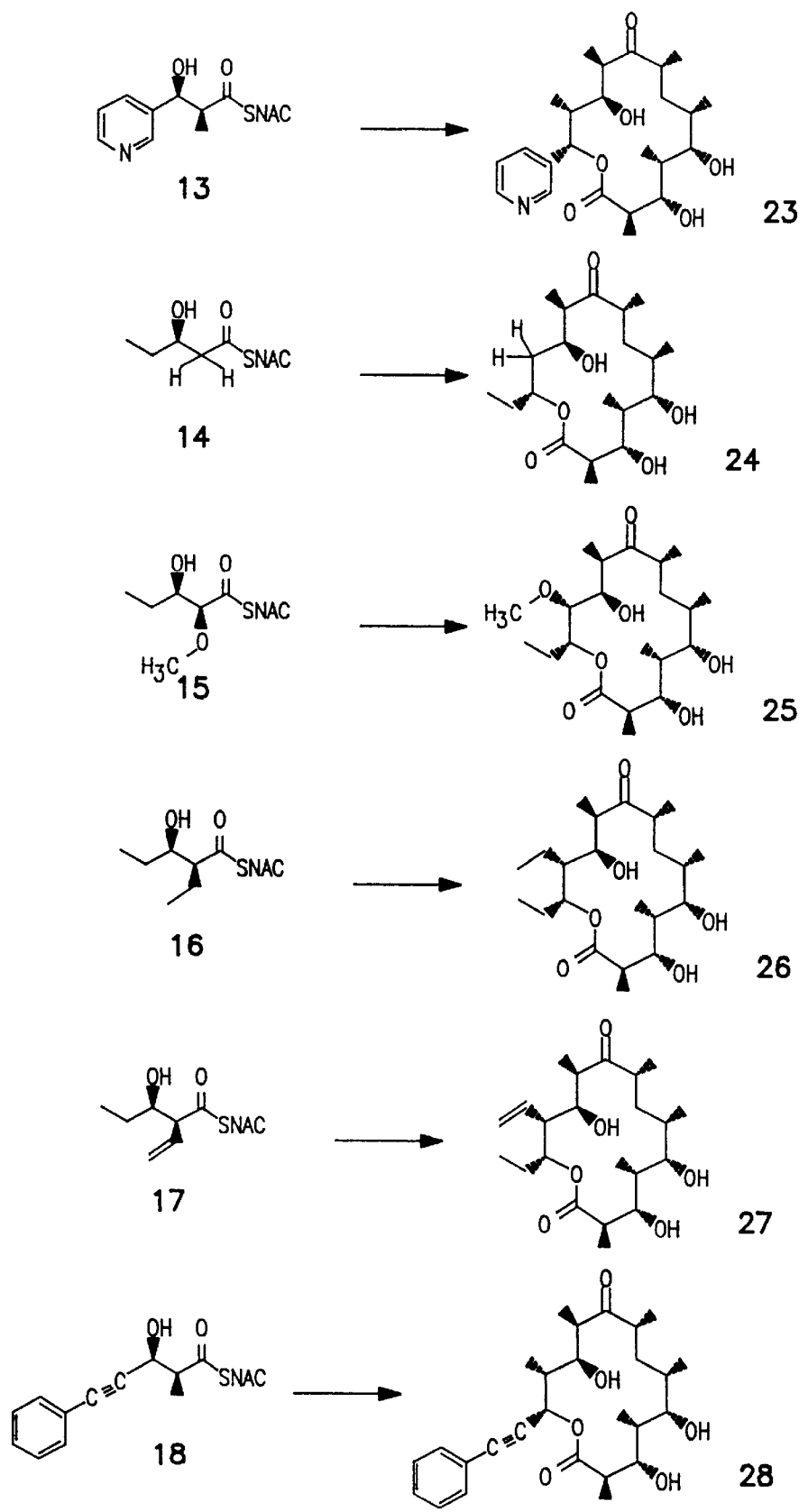

Diketides with the structures shown in FIGS. 2B and 2C as compounds 9–18 were administered to growing cultures of CH999/pJRJ2 under the conditions of Example 2. The products were those set forth in FIGS. 2B and 2C as compounds 19–28.

EXAMPLE 5

Steric Requirements

Using the same system set forth in Example 2, but substituting for compound 2 the three diastereomeric forms of the structure of formula 2 shown in FIG. 2A, synthesis of a polyketide in each case was not detected. Similarly, substituting for compound 12 its enantiomer at the 2-position, no synthesis of polyketide was detected.

EXAMPLE 6

Processing of the Polyketide Products

Figure 3:
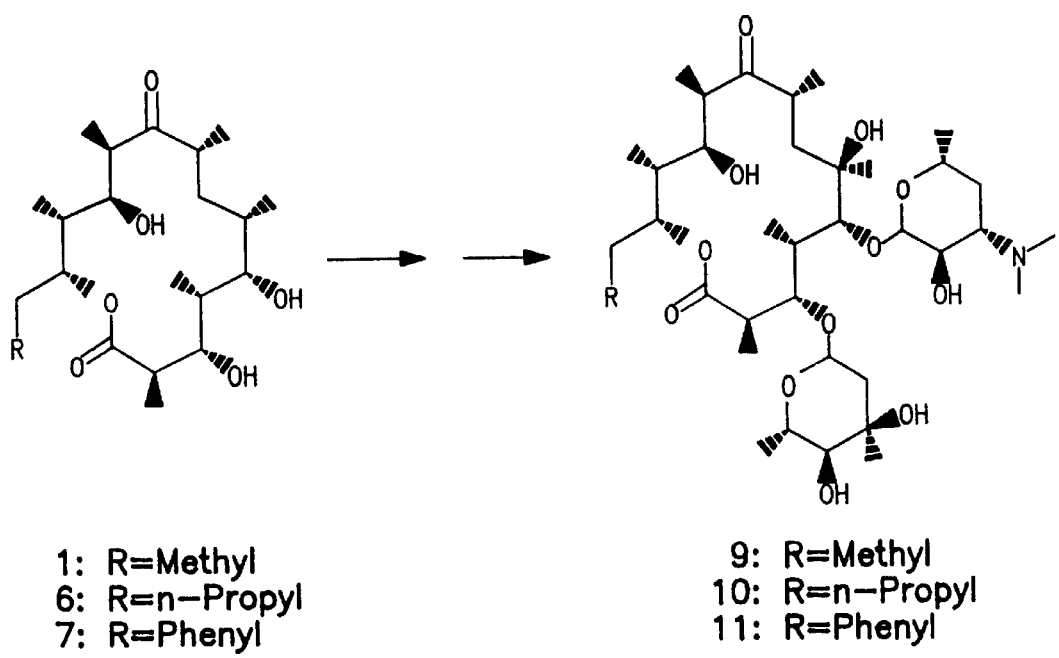
FIG. 3 shows the processing of 6-dEB derivatives to erythromycin-D derivatives.

The successful processing of unnatural intermediates by the "downstream" modules of DEBS prompted an experiment to determine whether the post-PKS enzymes in the erythromycin biosynthetic pathway might also accept unnatural substrates. In the natural producer organism, *Saccharopolyspora erythrae*, 6dEB undergoes several enzyme-catalyzed transformations. Oxidation at C6 and glycosylations at C3 and CS afford erythromycin D (formula 9 in FIG. 3) and subsequent transformations afford erythromycins A, B, and C. *S. erythrea* mutant (A34) (Weber, J.M. et al., *J. Bacteriol* (1985) 164:425–433) is unable to synthesize 6dEB. This strain produces no erythromycin when grown on R2YE plates (as judged by the ability of extracts to inhibit growth of the erythromycin-sensitive bacterium *Bacillus cereus*). However, when 6dEB (which has no antibacterial activity) is added to the culture medium, extracts exhibited potent antibacterial activity.

Samples of 6dEB derivatives 6 and 7 were assayed for conversion by this strain. Partially purified extracts demonstrated inhibition of B. cereus growth, and mass spectrometry was used to identify the major components of the extracts as formula 10 in FIG. 3 (from 6) and formula 11 (from 7).

In more detail, purified 6 and 7 (5 mg dissolved in 7.5 mL 50% aqueous ethanol) were layered onto R2YE plates (200 niL media/experiment) and allowed to dry. *S. erythrae*-A34 was then applied so as to give lawns. After 7 days of growth, the media were homogenized and extracted three times with 98.5:1.5 ethyl acetate:triethylamine. Pooled extracts from each experiment were dried over magnesium sulfate and concentrated. Extracts were partially purified by silica gel chromatography (gradient of methanol and triethylamine in chloroform). The partially purified extracts were examined by TLC and mass spectrometry. For antibacterial activity analysis, filter discs were soaked in 400 $\mu$M ethanolic solutions of erythromycin D, 10 and 11, as well as a concentrated extract from *S. erythrae* A34 which had been grown without addition of any 6-dEB analogs. Disks were dried and laid over freshly-plated lawns of Bacillus cereus. After incubation for 12h at 37°C., inhibition of bacterial growth was evident for all compounds but not for the control extract.

What is claimed is:
1. A polyketide which is selected from the group consisting of:
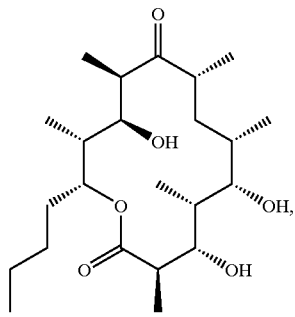
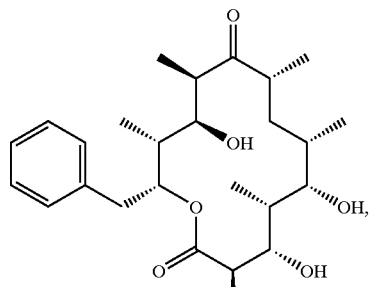
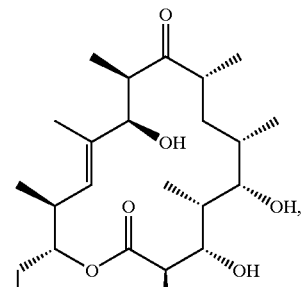
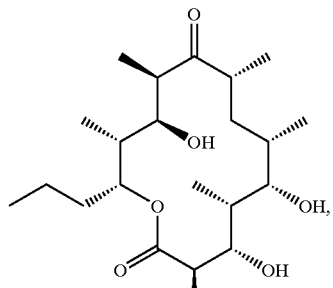
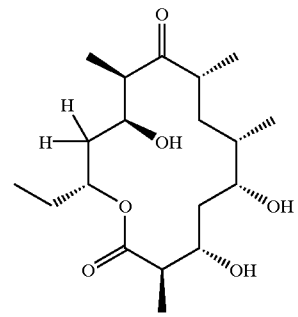
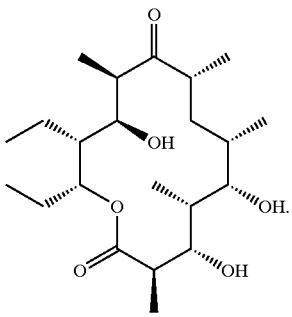
and
2. An antibiotic which is obtainable from the polyketide of claim 1 by a method which comprises treating said polyketide with a culture medium conditioned by *Saccharopolyspora erythraea*.
3. The polyketide of claim 1 which is selected from the group consisting of:
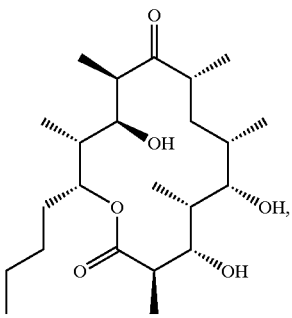
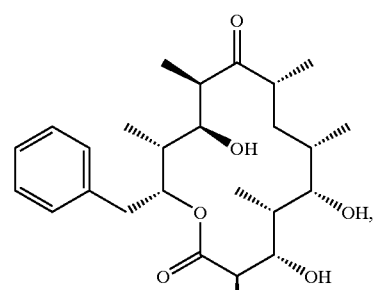
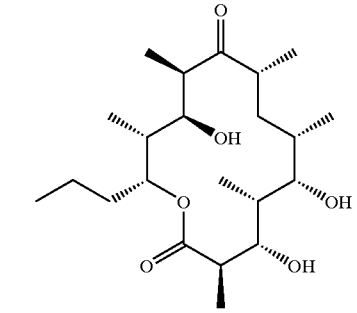
and

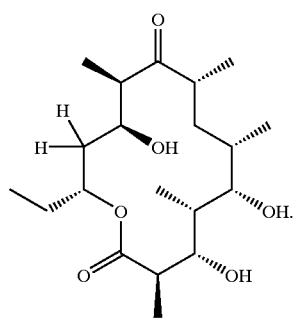
4. The polyketide of claim 3 which is selected from the group consisting of:
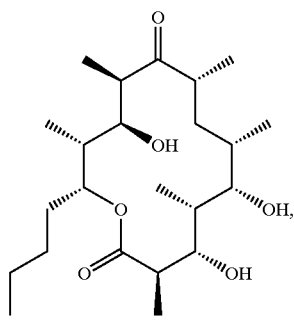
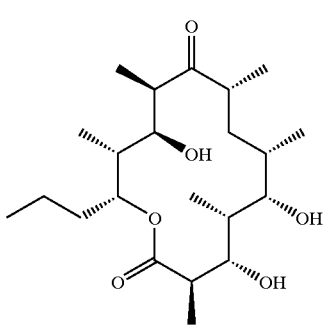
and
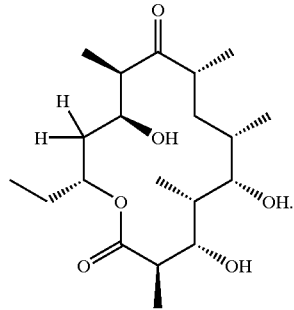
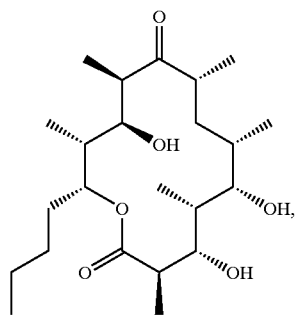
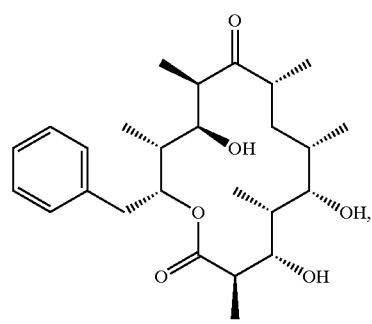
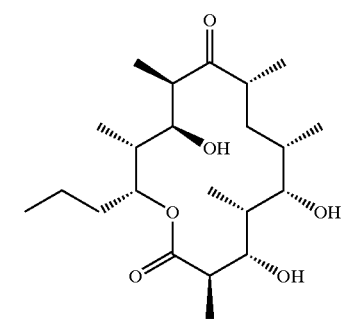
and
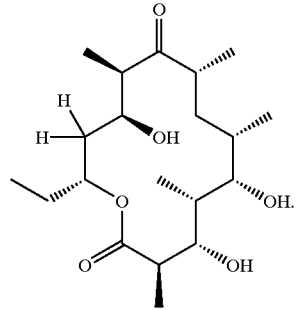
5. The antibiotic of claim 2 wherein the polyketide is selected from the group consisting of:
6. The antibiotic of claim 2 wherein the polyketide is selected from the group consisting of:

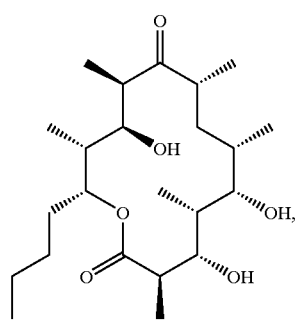
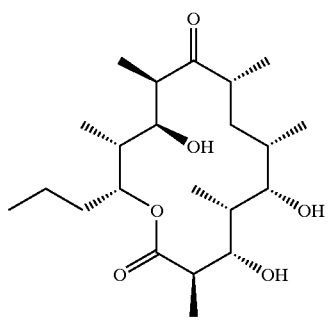
and
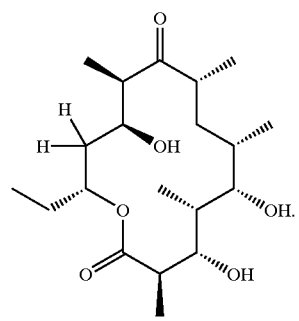
7. The antibiotic of claim 2 wherein the polyketide has the formula:
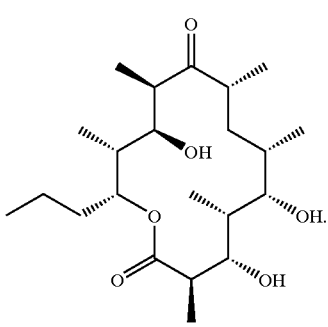
8. The polyketide of claim 1 having to formula:
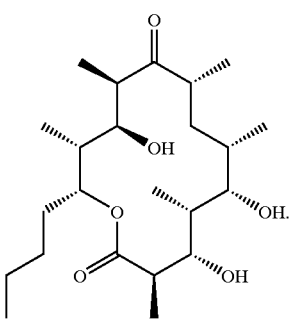
9. The polyketide of claim 1 having the formula:
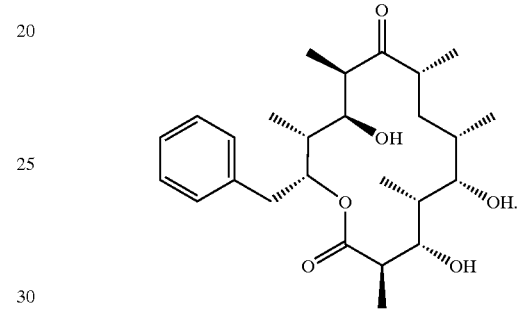
10. The polyketide of claim 1 having the formula:
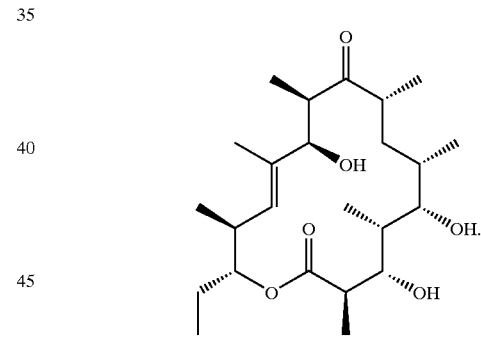
11. The polyketide of claim 1 having the formula:
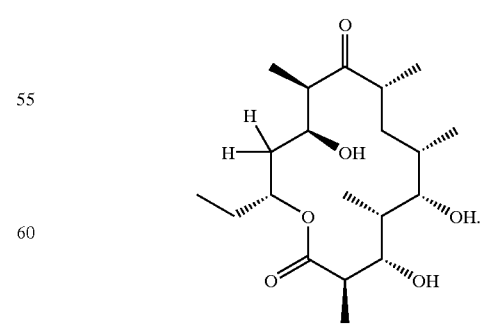

12. The polyketide of claim 1 having the formula:

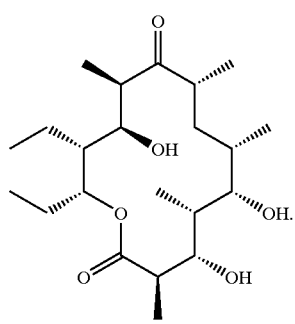

13. The antibiotic of claim 2 wherein the polyketide has the formula:

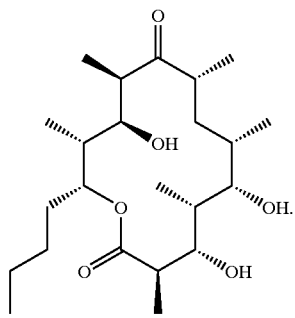

14. The antibiotic of claim 2 wherein the polyketide has the formula:

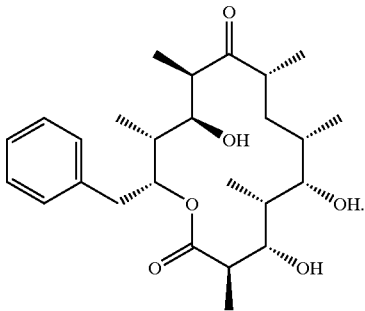

15. The antibiotic of claim 2 wherein the polyketide has the formula:

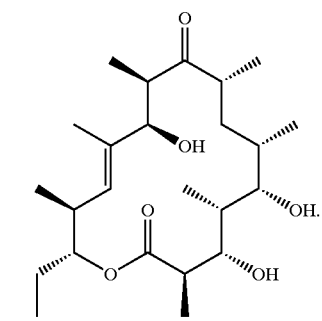

16. The antibiotic of claim 2 wherein the polyketide has the formula:

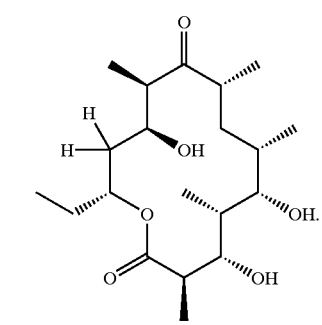

17. The antibiotic of claim 2 wherein the polyketide has the formula:

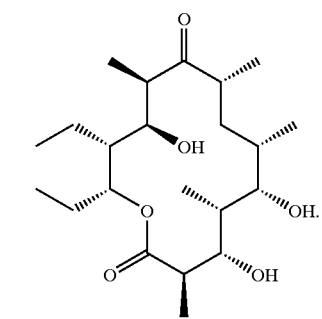

* * * * *